United States Patent [19]
Bugajski

[11] Patent Number: 5,738,668
[45] Date of Patent: Apr. 14, 1998

[54] COLOSTOMY BAG CLEANING DEVICE

[76] Inventor: Mark J. Bugajski, 338 E. Front St., Traverse City, Mich. 49684

[21] Appl. No.: 836,963

[22] PCT Filed: Aug. 14, 1996

[86] PCT No.: PCT/US96/13124

§ 371 Date: May 22, 1997

§ 102(e) Date: May 22, 1997

[87] PCT Pub. No.: WO97/06757

PCT Pub. Date: Feb. 27, 1997

Related U.S. Application Data

[63] Continuation-in-part of Ser. No. 514,934, Aug. 14, 1995, abandoned.

[51] Int. Cl.[6] ................................................ A61F 5/44
[52] U.S. Cl. ................................................ 604/332; 604/335
[58] Field of Search ................................ 604/277, 332, 604/335, 339; 222/529, 530; 251/243, 251, 326, 327; 15/320, 406, 407

[56] References Cited

U.S. PATENT DOCUMENTS

| | | | |
|---|---|---|---|
| 2,694,546 | 11/1954 | Goode | 251/243 |
| 3,612,053 | 10/1971 | Pratt | 128/283 |
| 3,635,375 | 1/1972 | Gaetke | 222/94 |
| 3,736,934 | 6/1973 | Hennessy | 128/283 |
| 3,910,274 | 10/1975 | Nolan | 128/227 |
| 4,134,404 | 1/1979 | Williams, Jr. | 128/283 |
| 4,194,506 | 3/1980 | Voorhies | 128/283 |
| 4,586,927 | 5/1986 | Jensen | 604/342 |
| 4,654,037 | 3/1987 | Fenton | 604/334 |
| 4,692,159 | 9/1987 | Kuzemchak | 604/277 |
| 4,941,878 | 7/1990 | Petrik | 604/105 |
| 5,096,503 | 3/1992 | Wellman | 134/22.18 |

FOREIGN PATENT DOCUMENTS

WO91/03217   3/1991   WIPO.

*Primary Examiner*—John G. Weiss
*Assistant Examiner*—David J. Cho
*Attorney, Agent, or Firm*—Young & Basile, P.C.

[57] ABSTRACT

A cleansing device (10) for use with a colostomy or other body waste bag. The device (10) includes a valve body (12) having a passage (14) and a gate valve (20) positioned in the passage (14), an elongated handle (34) controlling the gate valve (20), a hose (28) connected to the inlet (16) of the valve body passage and adapted to be secured to a source of irrigating water, and a tube (22) attached to the outlet (18) of the valve body passage including a main body portion (22a) and a nozzle portion (22b) bent backwardly with respect to the main body portion (22b) into the colostomy bag. The patient may grasp the valve body (12) with one hand to move the nozzle portion (22b) of the tube (22) upwardly into the discharge opening of the colostomy bag and may thereafter use the same hand to squeeze the handle (34) and direct a flow of irrigating fluid into the interior of the bag.

7 Claims, 3 Drawing Sheets

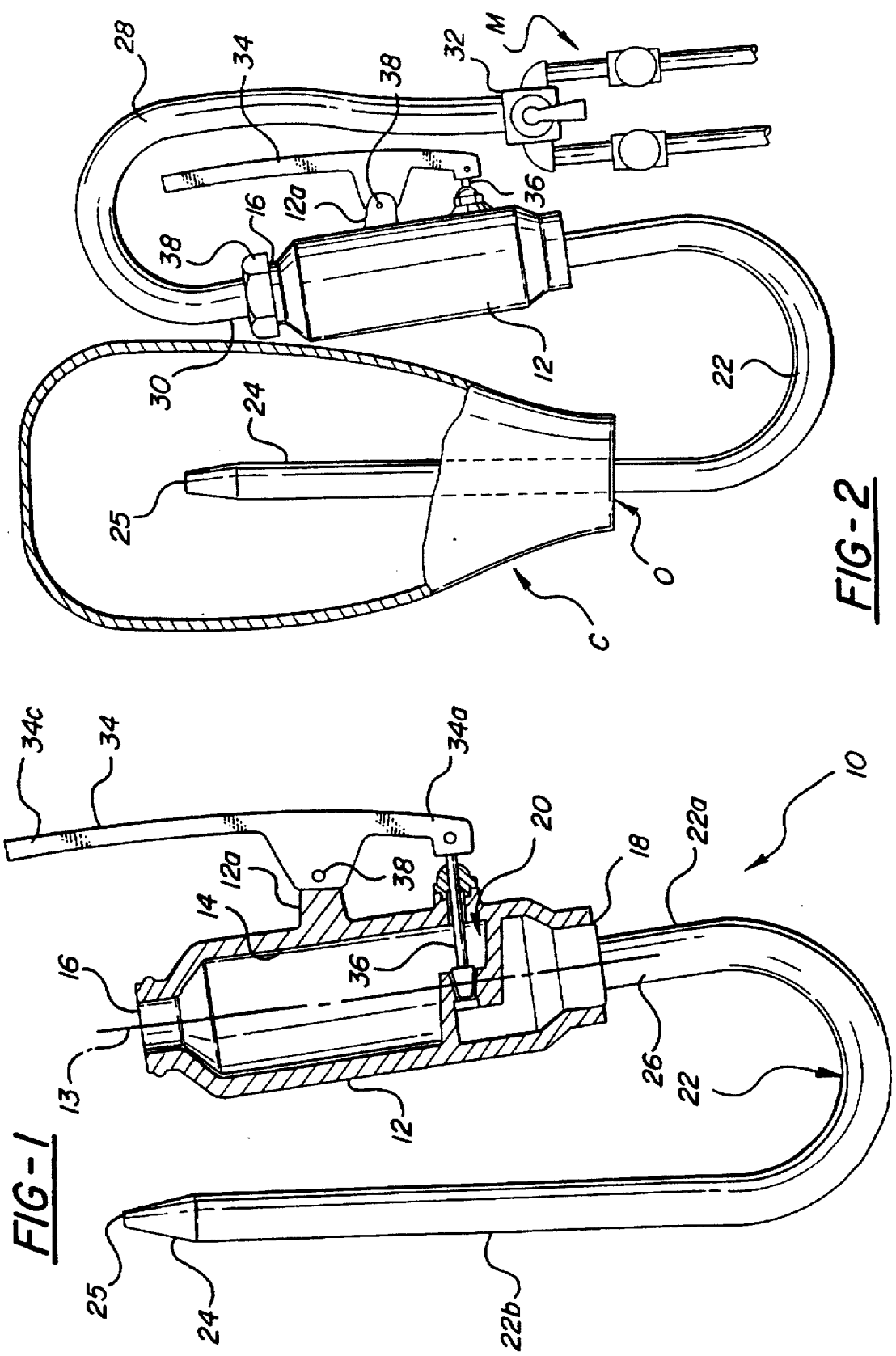

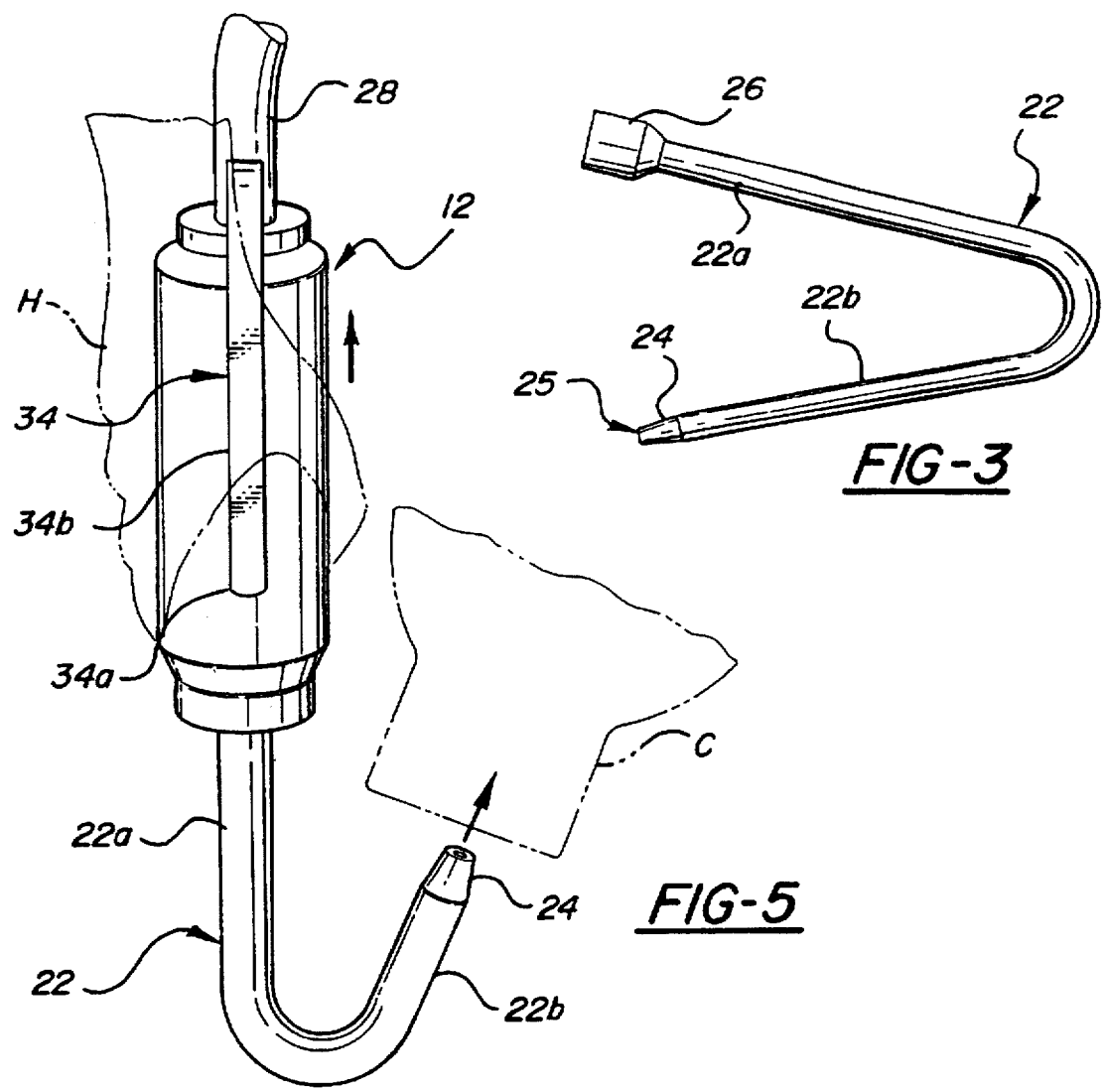
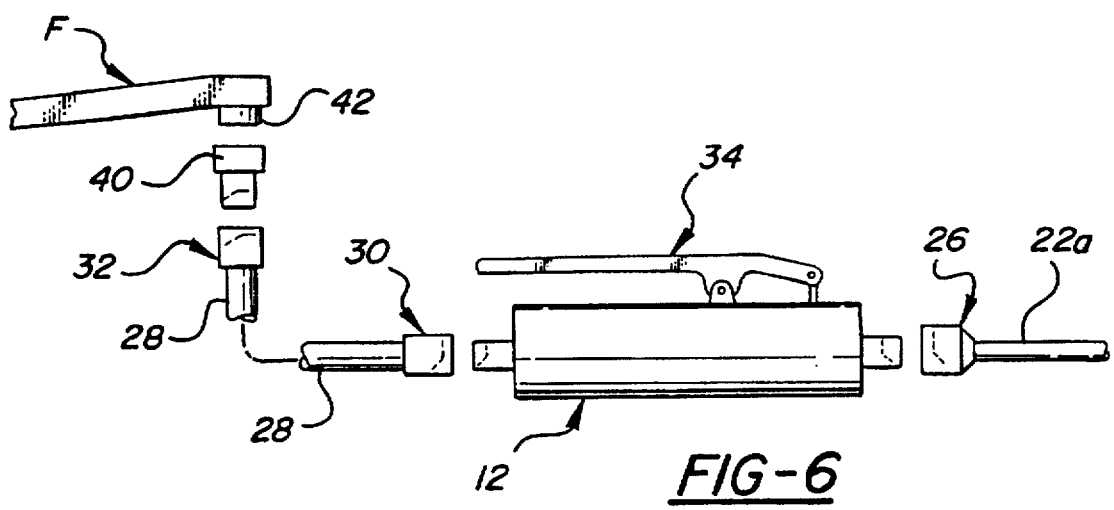

COLOSTOMY BAG CLEANING DEVICE

RELATED INVENTION

This application is a continuation in part of U.S. patent application Ser. No. 08/514,934 filed on Aug. 14, 1995 now abandoned and a 371 PCT/US96/13124 filed Aug. 14, 1996.

FIELD OF THE INVENTION

This invention concerns the field of fecal incontinence devices and, more particularly, to a device for and a method of effectively cleaning out said devices.

DESCRIPTION OF THE RELEVANT PRIOR ART

The use of incontinence devices such as ostomy pouches, colostomy bags, urostomy bags, as well as incontinence devices used in conjunction with natural body orifices, has been increasing in recent years. Patients with cancerous lesions, as well as other conditions of the gastrointestinal and urinary tracts, are often subjected to surgical procedures which remove parts of these systems, thus rendering the natural body orifices ineffective. It is frequently necessary to surgically create stoma or openings for the passage of, for example, fecal material. Thus, waste passing through these surgically created stoma must be collected via the now-familiar ostomy pouch or colostomy bag. Since the number of persons subjected to such surgical intervention has greatly increased in recent years, the problem of effectively cleaning these incontinence devices has become increasingly urgent.

A number of prior art devices are known for washing such incontinence devices. Examples include U.S. Pat. Nos.: 3,736,934; 4,194,506; 4,692,159; and 4,941,878. However, none of these prior art efforts are convenient or effective in use.

U.S. Pat. No. 4,941,878 discloses an ostomy pouch flusher comprising an elongate wand having a fluid inlet and discharge ports adjacent to opposite ends. A handle is provided on the wand adjacent to the inlet end. A framework of generally parallel rods extend along the wand and are spaced from each other to define therewith an open space for passage of a supply fluid and ostomy waste. The handle of the wand is connected via a hose to a faucet adapter for connection to a supply of cold water. No means is provided on this device for augmenting the flow rate of the water flowing therethrough except by means of adjusting the flow rate of the supply of cold water. Thus, the device has limited effectiveness.

U.S. Pat. No. 5,096,503 discloses an apparatus for washing body waste bags that have an opening. The device includes a diverter valve having an internally threaded spout to attach to a faucet. The diverter valve has a plunger, and a reduced size nipple adapted to be received in a small opening in a body waste bag. When the faucet is turned on, and the plunger is in a diverter open position, the water from the faucet flows normally through the diverter valve for regular use into the bag to wash it. When the plunger is in a closed position, the water flows through reduced sized openings to wash the bag with a reduced stream of water. The diverter valve remains on the faucet so that the faucet is available for normal use. Again, the device disclosed in this patent provides a cleansing stream of water, but the flow rate thereof is, if anything, actually less than that of water flowing from the faucet in its undiverted condition. Thus, the force of the stream used to clean the bag is no greater, and probably less, resulting in reduced effectiveness of the cleansing action thereof.

What is needed is a device for cleaning colostomy bags and other waste bags which is simple and easy to use, which may be used in conjunction with a readily available supply of hot and cold water, such as the typical faucet, but which is effective in cleaning the inside of the bag.

SUMMARY OF THE INVENTION

This invention relates to a device for cleansing a body waste bag of the type including an upper end adapted to be attached to a stoma to receive waste from the patient's body and a lower end including a discharge opening.

The device includes a valve body having an inlet and an outlet and defining a fluid passage extending within the body between the inlet and the outlet; an elongated flexible hose having an outlet fitting at one end for attachment to an inlet of the valve body and an inlet fitting at another end thereof for attachment to a source of running water; a valving device positioned in the passage and operative in response to movement of the valving device in the passage to control the flow of water through the passage; a handle positioned exteriorally of the valve body and mounted on the valve body for movement relative to the valve body; means operative in response to movement of the handle to move the valving device to control the flow of water through the passage; a tube having a V configuration including a main body portion and a nozzle portion angled with respect to the main body portion; an inlet fitting on the free end of the main body portion to facilitate attachment of the main body portion to the outlet of the valve body passage; and a nozzle at the free end of the nozzle portion having a tapered configuration to facilitate insertion of the nozzle portion into the discharge opening of the body waste bag. With this arrangement, and with the body waste bag attached to the stoma, the outlet fitting of the flexible hose attached to the inlet of the passage, and the inlet fitting of the main body portion of the tube attached to the outlet of the passage, the inlet fitting of the flexible hose may be attached to a source of running water, the nozzle portion of the tube may be passed upwardly into the discharge opening of the waste bag to position the nozzle within the bag, and the handle may be manipulated to move the valving device in a sense to open the passage and allow the flow of irrigating water from the source, through the hose, through the passage, and through the tube into the bag to cleanse the bag.

The invention also provides a method for cleansing a body waste bag of the type including an upper end adapted to be attached to a stoma to receive waste from the patient's body and a lower end including a discharge opening. The method is practiced utilizing a valve body having an inlet and outlet and defining a fluid passage extending within the body between the inlet and the outlet; an elongated flexible hose having an outlet fitting at one end attached to the inlet of the valve body and an inlet fitting at another end thereof for attachment to a source of running water; a valving device positioned in the passage and operative in response to movement of the valving device in the passage to control the flow of water through the passage; a handle positioned exteriorally of the valve body and mounted on the valve body for movement relative to the valve body; means operative in response to movement of the handle to move the valving device to control the flow of water through the passage; and a tube having a V configuration including a main body portion attached to the outlet of the valve body passage and a nozzle portion bent backwardly with respect to the main body portion and defining a nozzle at the free end of the nozzle portion having a tapered configuration to facilitate insertion of the nozzle portion into the discharge opening of the body waste bag. In carrying out the invention methodology, the body waste bag is attached to the stoma, the inlet fitting of the flexible hose is attached to a source of running water, the nozzle portion of the tube is passed upwardly into the discharge opening of the waste bag to position the nozzle within the bag, and the handle is manipulated to move the valving device in a sense to open the passage and allow the flow of irrigating water from the source, through the hose, through the passage, and through the tube into the bag to cleanse the bag.

According to a further feature of the invention methodology, the valve body is elongated and defines a central longitudinal passage; the handle is elongated, extends generally parallel to the central longitudinal passage, and is mounted for movement toward and away from the valve body in response to a squeezing movement exerted by a patient's hand wrapped around the valve body; and the main body portion of the tube extends generally parallel to the central longitudinal axis. With this arrangement a patient's hand wrapped around the valve body may squeeze the handle to regulate the flow of irrigating water through the valve body and may pull upwardly on the valve body to move the nozzle into the discharge opening of the bag.

BRIEF DESCRIPTION OF THE DRAWINGS

FIG. 1 is a side view of the cleaning device of the invention with certain elements thereof shown in cross-section;

FIG. 2 is a view of the cleaning device shown in operation to cleanse a colostomy bag;

FIG. 3 is a view of a wand or a tube utilized in the invention cleaning device;

FIG. 5 is a fragmentary view further illustrating the use of the cleaning device by a patient; and FIG. 6 is a schematic exploded view showing connectors for use with the invention cleaning device.

DETAILED DESCRIPTION OF THE PREFERRED EMBODIMENT

Figure 4:
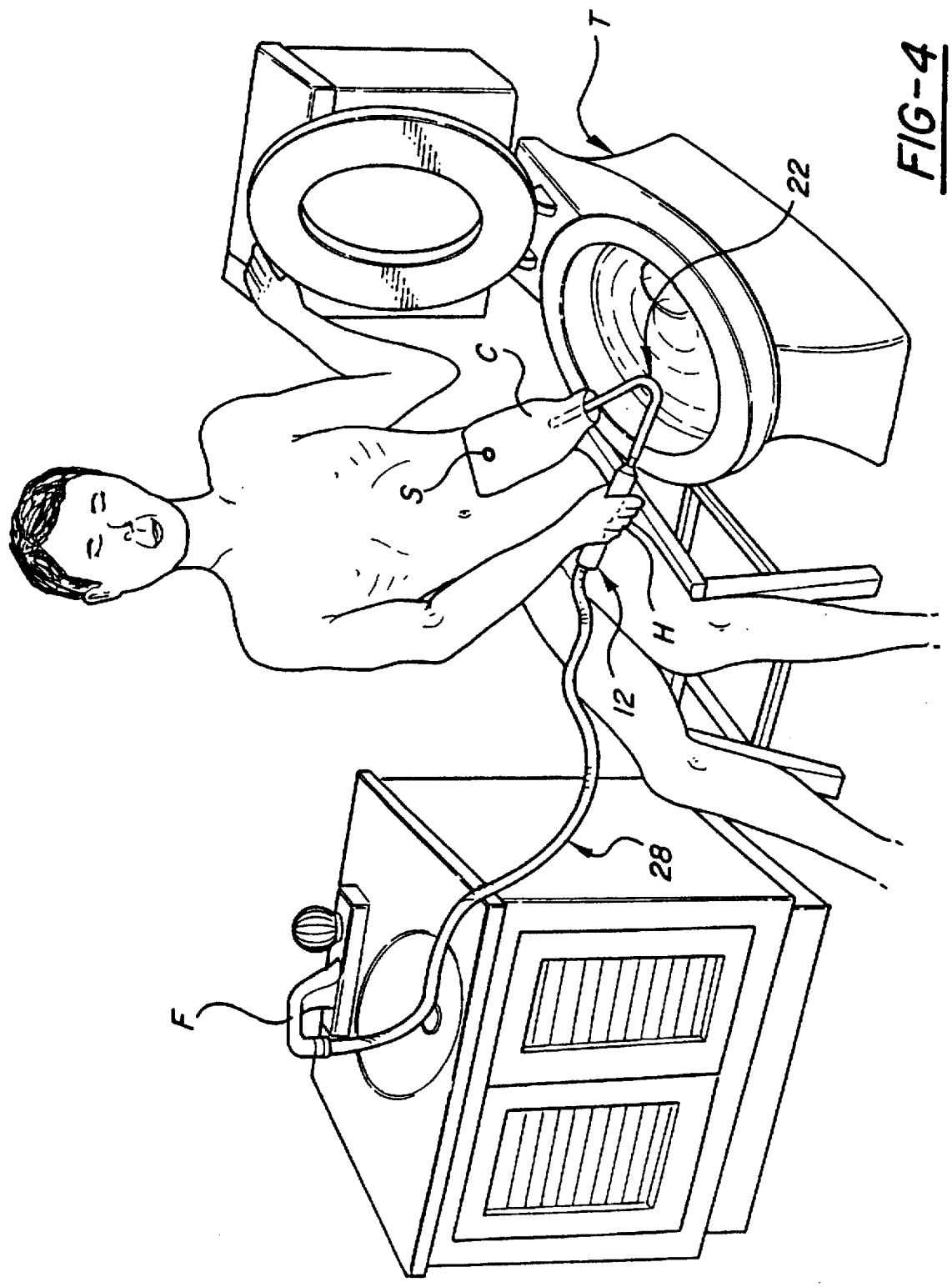
FIG. 4 is a view showing the use of the cleaning device by a patient.

The cleaning device 10 of the invention is intended for cleansing the inside of a body waste bag such as a colostomy bag C attached in known manner to a stoma S. The device 10 includes an elongated valve body 12 defining a central longitudinal axis 13 and further defining a fluid passage 14 extending therethrough. The fluid passage 14 has a fluid entrance or inlet 16 and a fluid exit or outlet 18 at opposite ends thereof. A gate valve, generally indicated at 20, is operatively associated with the fluid passage 14 such that operation of the gate valve will cause the flow rate of fluid passing through the fluid passageway 14 to either increase or decrease as desired. Gate valve 20 is operated by an elongated handle 34 positioned exteriorally of the valve body and extending generally parallel to central axis 13. One end 34a of handle 34 is pivotably attached to a valving device or plunger 36 controlling the gate valve and an intermediate portion 34b of the handle is pivotally attached at 38 to a lug structure 12a of the valve body so that downward pivotal movement of handle end 34c by a patient's hand H wrapped around the valve body 12 has the effect of squeezing the handle against the valve body to initially open valve 20 and thereafter, with further squeezing action, gradually increase the extent of valve opening to increase the flow rate of irrigating water through the passage.

Device 10 further includes a wand or tube 22 including a main body portion 22a and a nozzle portion 22b bent backwardly with respect to main body portion 22a to define a generally V configuration. The free end of nozzle portion 22b defines a nozzle 24 and free end 26 of main body portion 22a is removably attached to the fluid passage exit 18. Nozzle 24 has a diameter such that it may be inserted into the opening O of the colostomy bag C as can most clearly be seen in FIGS. 2 and 5. Nozzle 24 is tapered and defines a reduced diameter opening 25. Thus, water flowing through the tube 22 will exit via nozzle 24 which, because of the constriction resulting from the reduced diameter opening 25, will cause the flow rate of water to increase and become turbulent, thus improving its cleansing action. The tapered shape of the nozzle and the small size of opening 25 helps the operator to direct the water flow in the desired direction within the bag.

Cleansing device 10 further includes a hose 28 which is removably attachable to the fluid entrance 16 of nozzle body 12. As can be seen in FIG. 2, hose 28 has a first end 30 which is removably attached to fluid entrance 16 and a second end 32 which is removably attached to a source of hot and cold running water, such as a mixing valve M (FIG. 2) or a sink faucet F (FIG. 4). A conventional threaded connector may be supplied on the end 32 of hose 28 to facilitate attachment to valve M or faucet F or a quick connect (not depicted) may be used. Alternatively, the valve M or faucet F may be supplied with an adapter fitting to receive the end 32 of the hose. A quick connect 38 may also be used to attach the first end 30 of the hose to the fluid entrance 16. Furthermore, O-rings are preferably provided at the fluid exit 18 and the fluid entrance 16 so that water pressures of up to 350 pounds per inch may be contained inside the device 10.

Tube 22 is preferably disposable and is preferably formed of a plastic material that is sufficiently rigid to hold any shape to which it is bent but yet flexible enough to allow selective reconfiguration of the V shape of the tube. For example, tube 22 may be formed of a flexible polymeric material such as PVC. It is highly desirable that the tube 22 be fabricated of lightweight materials because many patients who have incontinence bags are otherwise handicapped and/or weak. Tube 22 may vary in size so as to be useable with different sorts of body waste bags. Because the tube 22 is flexible, it may be directed at various angles into the interior of the bag C thus improving the cleansing action.

In use, device 10 is attached to mixing valve M or faucet F by attaching the respective ends 30, 32 of the hose 28 to the fluid entrance 16 of valve body 12 and to the valve M or faucet F. The nozzle 24 is then positioned inside the colostomy bag C. The taps associated with the valve M or faucet F are then adjusted to provide the desired temperature and quantity of water. The gate valve 20 is then opened by squeezing elongated handle 34 against valve body 12, thus causing the water to flow through fluid passage 14. By suitable operation of the gate valve 20, the flow rate of the water passing through passage 14 may be controlled to provide a greater or lesser flow rate as desired.

Thus, the flow rate of the water available for cleansing the interior of the colostomy bag C may be advantageously adjusted so that the water emanating from the nozzle 24 will strike the inside surface of the bag C at an augmented rate, thus considerably improving the cleansing action. Because of this feature, a relatively small amount of water from valve M or faucet F may be used for effective cleaning of the inside of the bag.

The device of the present invention is very easy to use and very effective. It may be used by the patient, or by an attendant. Furthermore, as seen in FIG. 4, it is easy for the patient to clean the bag with the bag in place on the patient, thus eliminating the discomfort and problems associated with constant attachment and reattachment of the incontinence bag to the stoma. By attaching the device to a mixing valve or faucet located proximate a toilet T, the contents of the bag may be flushed directly into the toilet, thus avoiding contamination of the sink area. Because the device is so easy to use and effective, body waste bags may be cleaned more thoroughly and more often, thus greatly contributing to the patient's comfort, and the cleanliness of the bag environment.

With specific reference to FIGS. 4 and 5, the invention device allows simple one-handed operation even by patients suffering from arthritic or other physically debilitating conditions. Specifically, the single hand H of the patient may be wrapped around valve body 12 and around handle 34 whereafter the patient may position the nozzle 24 beneath the discharge opening of the bag C and thereafter pull upwardly on the valve body 12 to move the nozzle portion 22b into the bag, whereafter the patient may squeeze the handle 34 downwardly to begin and thereafter control the rate of flow of irrigating water through the device. The device allows the contents of the bag to be readily emptied into a toilet in a totally hygienic manner and even the patient's hand is situated away from the discharge of the bag contents so that there is no contamination even of the patient's hand. Simple and hygienic one-hand operation, even by arthritic patients, is thus made possible by the invention device.

The device of the present invention may take other forms and designs than those depicted and described herein. For example, the exact configuration of the valve body may be different from that depicted. Furthermore, the V configuration of the tube may vary from the specific shapes illustrated. It will be understood that the attachment of tube 22 to the outlet of the valve body, the attachment of hose 28 to the inlet of the valve body, and the attachment of hose 28 to mixing valve M or faucet F may be accomplished utilizing various known connecting devices such as threaded connectors, snap connectors, or quick connectors. For example, with reference to FIG. 6, fittings or ends 30, 32, and 26 may each comprise a female lock stop connector coacting with a male lock stop connector provided respectively on opposite ends of the valve body and on faucet F. The lock stop fitting in each case includes an inside ledge on the female connector coacting with an outside ledge on the male connector in response to relative pushing and turning movement. The male lock stop connector on faucet F may be provided on an adaptor 40 threaded onto a threaded nipple 42 on the faucet following removal of the usual aerator screen.

I claim:

1. A device for cleansing a body waste bag of the type including an upper end adapted to be attached to a stoma to receive waste from the patient's body and a lower end including a discharge opening, the device including:

a valve body having an inlet and an outlet and defining a fluid passage extending within the body between the inlet and the outlet;

an elongated flexible hose having an outlet fitting at one end for attachment to the inlet of the valve body and an inlet fitting at another end thereof for attachment to a source of running water;

a valving device positioned in the passage and operative in response to movement of the valving device in the passage to control the flow of water through the passage;

a handle positioned exteriorly of the valve body and mounted on the valve body for movement relative to the valve body;

means operative in response to movement of the handle to move the valving device to control the flow of water through the passage;

a tube having a V configuration including a main body portion and a nozzle portion bent backwardly with respect to the main body portion;

an inlet fitting on the free end of the main body portion to facilitate attachment of the main body portion to the outlet of the valve body passage; and a nozzle at the free end of the nozzle portion having a tapered configuration to facilitate insertion of the nozzle portion into the discharge opening of the body waste bag;

whereby, with the body waste bag attached to the stoma, the outlet fitting of the flexible hose attached to the inlet of the passage, and the inlet fitting of the main body portion of the tube attached to the outlet of the passage, the inlet fitting of the flexible hose may be attached to a source of running water, the nozzle portion of the tube may be passed upwardly into the discharge opening of the waste bag to position the nozzle within the bag, and the handle may be manipulated to move the valving device in a sense to open the passage and allow the flow of irrigating water from the source, through the hose, through the passage, and through the tube into the bag to cleanse the bag.

2. A device according to claim 1 wherein:

the valve body is elongated and defines a central longitudinal axis; and the handle is elongated, extends generally parallel to the central longitudinal axis, and is mounted for movement toward and away from the valve body in response to a squeezing movement exerted by a patient's hand wrapped around the valve body.

3. A device according to claim 2 wherein the handle is mounted for pivotal movement on the valve body.

4. A device according to claim 2 wherein the inlet and outlet are at opposite ends of the valve body and the passage extends through the valve body generally parallel to the central longitudinal axis.

5. A device according to claim 2 wherein, with the body outlet positioned downwardly, the main body portion of the tube extends downwardly away from the valve body generally parallel to the central longitudinal axis of the valve body and the nozzle portion angles upwardly from the main body portion whereby upward movement of the valve body moves the nozzle upwardly into the discharge opening of the body waste bag.

6. A method for cleansing a body waste bag of the type including an upper end adapted to be attached to a stoma to receive waste from the patient's body and a lower end including a discharge opening, the method including:

providing a valve body having an inlet and outlet and defining a fluid passage extending within the body between the inlet and the outlet, an elongated flexible hose having an outlet fitting at one end attached to the inlet of the valve body and an inlet fitting at another end thereof for attachment to a source of running water, a valving device positioned in the passage and operative in response to movement of the valving device in the passage to control the flow of water through the passage, a handle positioned exteriorly of the valve body and mounted on the valve body for movement relative to the valve body, means operative in response to movement of the handle to move the valving device to control the flow of water through the passage, a tube having a V configuration including a main body portion attached to the outlet of the valve body passage and a nozzle portion bent backwardly with respect to the main body portion, and a nozzle at the free end of the nozzle portion having a tapered configuration to facilitate insertion of the nozzle portion into the discharge opening of the body waste bag;

attaching the body waste bag to the stoma;

attaching the inlet fitting of the flexible hose to a source of running water;

passing the nozzle portion of the tube upwardly into the discharge opening of the waste bag to position the nozzle within the bag; and manipulating the handle to move the valving device in a sense to open the passage and allow the flow of irrigating water from the source, through the hose, through the passage, and through the tube into the bag to cleanse the bag.

7. A method according to claim 6 wherein the valve body is elongated and defines a central longitudinal passage; the handle is elongated, extends generally parallel to the central longitudinal axis, and is mounted for movement toward and away from the valve body in response to a squeezing movement exerted by a patient's hand wrapped around the valve body; and the main body portion of the tube extends generally parallel to the central longitudinal axis whereby a patient's hand wrapped around the valve body may pull upwardly on the valve body to move the nozzle opening into the discharge opening of the bag and may thereafter squeeze the handle to direct a flow of irrigating water through the valve body and into the bag.

\* \* \* \* \*